United States Patent [19]

Udaka et al.

[11] Patent Number: 4,656,037

[45] Date of Patent: Apr. 7, 1987

[54] SPF-100 AND PROCESS FOR THE PREPARATION THEREOF

[75] Inventors: Shigezo Udaka, Aichi; Hideo Ueyama, Hyogo; Junichi Taniguchi, Osaka; Keiji Adachi, Hyogo, all of Japan

[73] Assignees: Udaka, Shigezo, Aichi; Furukawa Keiichiro, Tokyo; Shikibo Ltd., Osaka, all of Japan

[21] Appl. No.: 746,514

[22] Filed: Jun. 19, 1985

Related U.S. Application Data

[63] Continuation-in-part of Ser. No. 631,774, Jul. 17, 1984, abandoned.

[30] Foreign Application Priority Data

Aug. 1, 1983 [JP] Japan ............................... 58-139384
Aug. 1, 1983 [JP] Japan ............................... 58-139385
Apr. 13, 1984 [JP] Japan ............................... 59-072865
Apr. 13, 1984 [JP] Japan ............................... 59-072866

[51] Int. Cl.$^4$ ........................ A61K 35/74; C12P 1/04
[52] U.S. Cl. ................................... 424/118; 424/116; 435/170
[58] Field of Search ................ 424/116, 118; 435/169, 435/170

*Primary Examiner*—Jerome D. Goldberg
*Attorney, Agent, or Firm*—Browdy and Neimark

[57] ABSTRACT

Penicillin or related substances are added during the course of the cultivation of a streptococcus to recover SPF-100 from the culture broth. SPF-100 exhibits a broad range of molecular weight and may be classified into SPF-1 and SPF-2.

SPF-100 has a direct cancericidal effect and an immunoactivation effect.

2 Claims, 6 Drawing Figures

SPF-100 AND PROCESS FOR THE PREPARATION THEREOF

This application is a continuation-in-part of parent, copending application Ser. No. 631,774, filed July 17, 1984, now abandoned in favor of the present case.

BACKGROUND OF THE INVENTION

1. Field of the Invention

This invention relates to a process for culturing streptococci which comprises discharging an active ingredient of the bacterium outside the body.

More particularly, this invention relates to a process which comprises adding pencillin or related substances during the course of the cultivation of the bacterium to discharge a substance produced by the bacterium outside the body thereby accumulating the product in the medium.

Furthermore it is an object of the present invention to provide SPF-100 which exhibits a direct cancericidal effect in mice and an immunoactivation effect.

2. Description of the Prior Art

Attenuated vital *Streptococcus pyogenes* has been already used to formulate a carcinostatic.

In addition there have been known a process which comprises grinding bodies of *S. pyogenes*, extracting an active ingredient therefrom with water or a saline solution and adding an organic solvent to thereby recover a tumoricidal ingredient as a precipitate (cf. Japanese Patent Publication No. 1647/1963) and another process which comprises bacteriolyzing *S. pyogenes* with a lysokinase such as lysozyme or cellulase or a proteinase and fractionating the active fraction as an aqueous phase (cf. British Pat. No. 1163865).

As described above, it has been well known that streptococci themselves or some ingredients thereof would exhibit a tumoricidal activity. However the conventionally known substances are merely bacterial bodies or soluble or insoluble polymer constituents of cells. In order to isolate an active ingredient from a bacterium, it is necessary to bacteriolyze or mechanically grind the bacterium to fractionate the whole. These treatments might complicate the purification so that the isolation of an active ingredient is very difficult. An example of an active ingredient which has been actually isolated and determined is a protein of 150,000 in molecular weight (cf. Japanese Patent Publication No. 43841/1973).

SUMMARY OF THE INVENTION

We have considered that purification of various bacterial products produced by streptococci might be simplified to a considerable extent by discharging these products outside the bodies during the course of the cultivation and that more useful physiologically active substances may be further found thereby. As a result of our researches from the abovementioned viewpoint, we have succeeded in discharging a bacterial product outside the body by adding penicillin during the course of the cultivation.

Thus this invention provide a process which comprises adding penicillin or related substances at an appropriate point during the course of the cultivation and isolating SPF-100 from the culture broth thus obtained.

SPF-100 is a novel substance which has not been known hitherto. It exhibits a broad range of molecular weight and may be classified into SPF-1 and SPF-2 depending on its molecular weight.

BRIEF DESCRIPTION OF THE DRAWINGS

FIG. 1 shows an ultraviolet absorption spectrum of a 0.1% aqueous solution of SPF-100, while

FIG. 3 shows an ultraviolet absorption spectrum of a 3.3% aqueous solution of SPF-1, while

FIG. 5 shows an ultraviolet absorption spectrum of a 0.2% aqueous solution of SPF-2, while

DETAILED DESCRIPTION OF PREFERRED EMBODIMENTS

Figure 1:
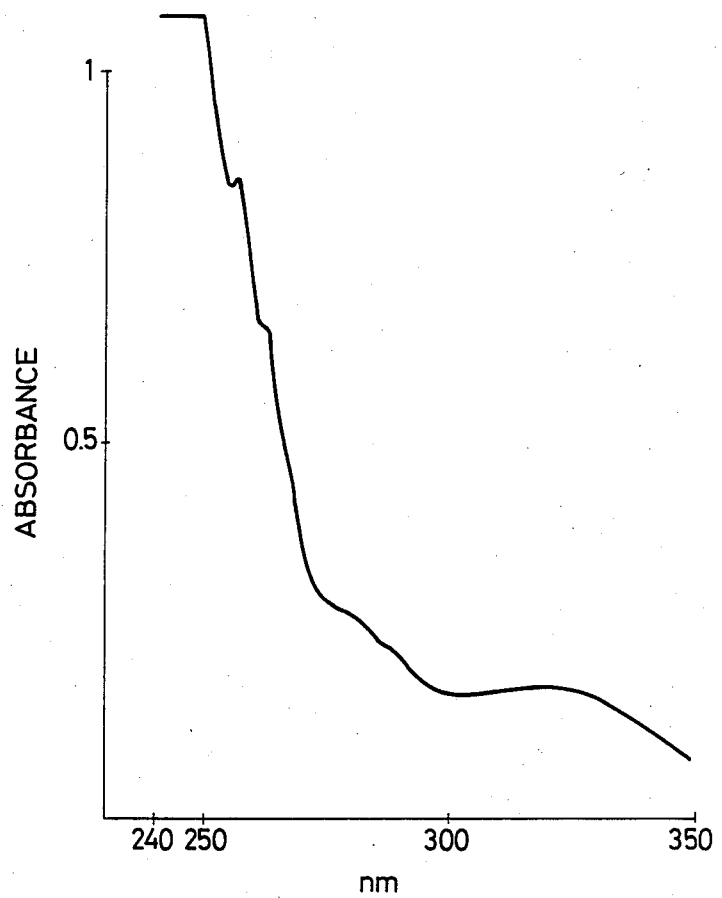

SPF-100 exhibits a direct cancericidal effect in mice and an immunoactivation effect.

In the process of the present invention, a bacterial product is discharged outside the body and present in the medium. Therefore it may be isolated by a fairly simplified method, i.e., by filtering off the bacterial bodies and purifying the filtered culture broth.

There has been known a process which comprises culturing a streptococcus and attenuating the obtained bacterium by treating with penicillin. However there has never been reported a process which comprises discharging a bacterial product outside the body by adding penicillin during the course of the cultivation.

In the process of the present invention any of the streptococci may be used. Examples of the bacteria are as follows:

*Streptococcus pyogenes* ATCC 21060;
*Streptococcus sp.* ATCC 21597;
*Streptococcus pyogenes* ATCC 21546;
*Streptococcus pyogenes* ATCC 21547; and
*Streptococcus pyogenes* ATCC 21548.

Natural media such as meat extract medium, yeast extract medium and brain heart infusion medium (BHI medium) have been frequently used although general media containing carbon or nitrogen sources may be used so long as the streptococci would be grown effectively therein.

Streptococci may be grown under appropriate conditions i.e., at a pH of 6.0 to 8.0 (preferably 6.8 to 7.2) and a temperature of 30° to 40° C. (preferably, 35° to 37° C.). Generally an araerobic and static culture is employed although some other method including stirred culture may be employed.

According to the present invention, penicillin or related substances are added at an appropriate point during the course of the cultivation to discharge various useful substances produced by the bacterium outside the body, thereby accumulating these products in the medium.

Any related substance which has been known to exhibit a similar effect to that of penicillin may be used, although usually penicillin G or cephalosporin C is employed. Penicillin G is used in an amount of 100 to 7000 units/ml of the medium and preferably 1000 to 5000 units/ml of the medium. Cephalosporin C is used in an amount of 10 to 4000 μg/ml of the medium and preferably 100 to 1500 μg/ml of the medium.

Penicillin or related substances may be added 3 to 15 hours, preferably 5 to 10 hours, after the initiation of the logarithmic growth phase when the bacterium is cultured at 37° C. Continuation of the cultivation for 1 to 20 hours, preferably 5 to 15 hours thereafter would make it possible to accumulate a large amount of a bacterial product in the medium.

The culture broth thus obtained is centrifuged to remove the bacterium and ammonium sulfate is added to the filtrate. After recovering fractions of 50 to 90% in the degree of saturation, the obtained precipitate is dissolved in a buffer solution containing a stabilizer.

The obtained solution containing SPF-100 may be stored in a frozen or lyophilized form. This substance may be further purified by contacting with an ion exchanger or a gel filtration materials. Ion exchangers such as an ion exchange resin, an ion exchange cellulose or ion exchange Sephadex (a product of Pharmacia AB) and gel filtration materials such as Toyopearl HW-50F or HW-50SF (a product of Toyo Soda Kabushiki Kaisha) or Sephadex (a product of Pharmacia AB) may be used. In addition calcium phosphate gel may be used as such, although it is convenient to use it in the form of hydroxylapatite. An aqueous solution of the substance as obtained by the abovementioned way may be allowed to pass through a column in which these ion exchangers or gel filtration materials are charged to an appropriate rate. Alternately, the aqueous solution may be introduced into a container containing these ion exchangers or gel filtration materials at once to contact the active substance with the treating materials. Elution may be carried out with a buffer solution of an appropriate saline concentration and pH value. Two or more ion exchangers, gel filtration materials or calcium phosphate gel may be combined if desired. For example, a solution of SPF-100 may be eluted by contacting with DEAE Sephadex and then the eluate may be further eluted by contacting with Toyopearl HW50F or 50SF to thereby obtain an improved purification effect.

The SPF-100 of the present invention obtained in Example 8 as will be described hereinafter is a peptide-like substance and becomes a pale yellow powder when lyophilized.

Physicochemical properties of the tumoricidal composition SPF-100 are as follows:

1. Elemental analysis

C: 46.42 to 43.69%, H: 5.94 to 4.85%, N: 11.42 to 9.50%, O: 33.82 to 39.69% and Ash: 2.40 to 2.27%.

2. Molecular weight

Approximately 500 to 25,000 as determined by gel filtration.

3. Decomposition point

It turns to brown at 160° C. and to black at 200° C. and decomposes.

4. Specific rotation $[\alpha]_D^{20} = +45.0°$ (c=1.00).

5. Ultraviolet absorption spectrum

FIG. 1 shows an ultraviolet absorption spectrum of a 0.1% aqueous solution, which is characterized by the absorptions at 257, 265, 280, 287 and 325 nm.

6. Infrared absorption spectrum

Figure 2:
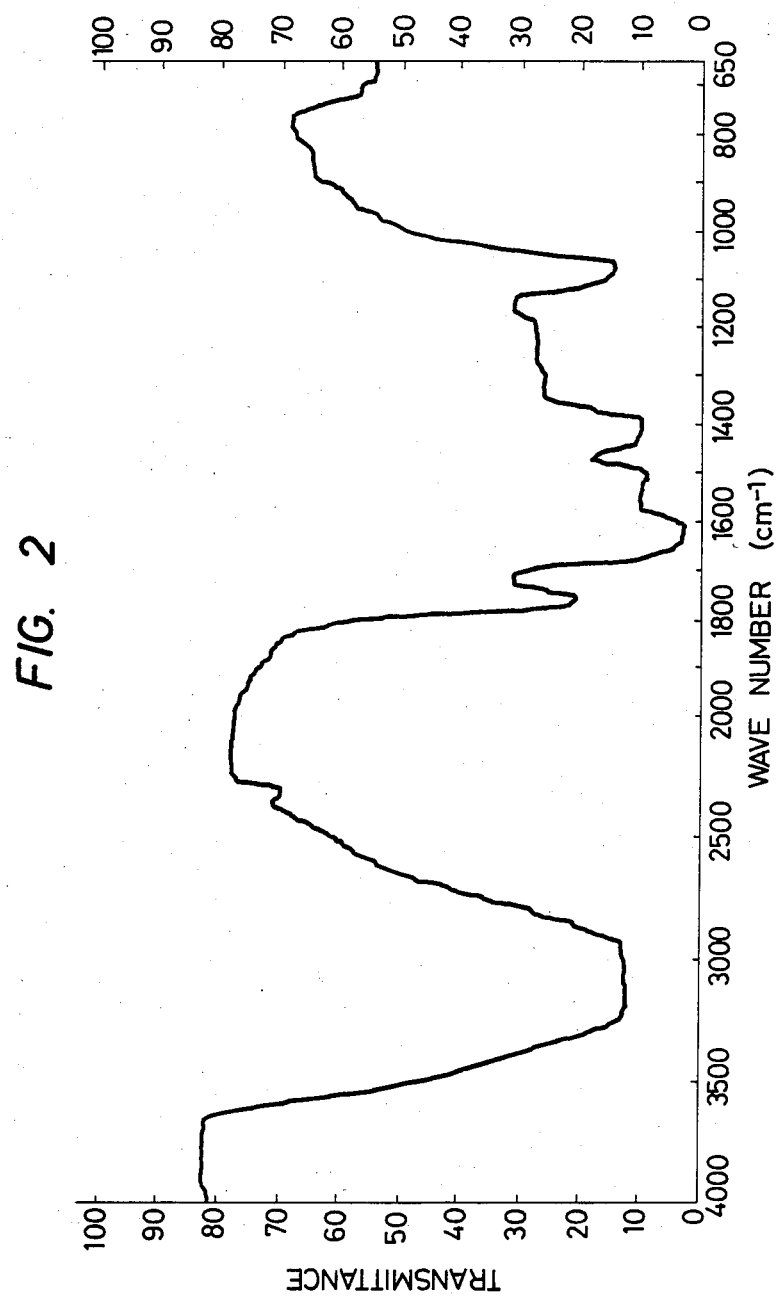
FIG. 2 shows an infrared absorption spectrum of SPF-100.

FIG. 2 shows an infrared absorption spectrum.

7. Solubility in solvents

It is soluble in water, partly soluble in methanol and ethanol and hardly or not soluble in solvents including n-butanol, isobutanol, n-propanol, n-hexane, chloroform, acetone, methyl isobutyl ketone and ethyl ether.

8. Acidity

The pH value of a 1.0% aqueous solution is 6.5.

9. Form

Pale yellow powder

10. Color reactions ninhydrin reaction: +,
biuret reaction: +,
Molisch reaction: −,
Dische reaction: −,
anthrone reaction: −, and
cysteine sulfate reaction: −.

11. Stability

It can be stabilized by adding L-cysteine, dithiothreitol (DTT), glycerol, albumin, globulin, α- and β-cyclodextrin, $(NH_4)_2SO_4$, common salt or the like.

Now Examples of the embodiment of the present invention will be given.

In the following examples, the activity unit of SPF-100 was determined by the Udaka's method, cf. Journal of Antibiotics, Vol. 35, No. 10, 1319 to 1325 (October 1982). The activity was bioassayed by the use of a macromolecule-permeable mutant of a colon bacillus MP-2 (FERM-P5432) (cf. Agric. Biol. Chem., Vol. 43, p. 371 (1979)) with the guidance of the antibacterial activity against MP-2.

That is to say, a medium (i.e. M3 medium) consisting of 1.75% of Bact Antibiotic medium 3 (a product of Difco) and 1.3% of agar was sterilized by heating to 120° C. for 15 min. Then 20 ml portions of the medium were poured into Petri dishes and allowed to cool to prepare plate media.

On the other hand, a medium consisting of 0.5% of peptone, 0.5% of meat extract, 0.3% of NaCl and 0.8% of agar was sterilized by heating to 120° C. for 15 min. Then it was placed in a thermostat at 42° C. When the temperature of the medium reached to 42° C., MP-2 which had been clutured at 37° C. for 17 hours was added to the medium at a concentration of $10^4$ cells/ml. Two ml of the medium was collected with a pipet and added to the surface of the M3 medium which has been previously prepared. Then the added medium was immediately spreaded homogeneously and solidified. A test solution containing the SPF-100 was appropriately diluted. A paper disc (φ8 mm; a product of Toyo Roshi Co., Ltd.) was wetted with the solution thus obtained. Subsequently this paper disc was placed on the plate prepared above and cultured for 17 hours at 37° C. to determine the diameter of the inhibition zone resulting from the SPF-100. Then the concentration of the SPF-100 at which the diameter of the inhibition zone was 10 mm was defined as one unit (1 u).

EXAMPLE 1

9 l of medium A having the following composition was employed:

| meat extract | 1%, |
|---|---|
| polypeptone | 1%, |
| yeast extract | 0.25%, |
| casamino acids | 0.25% and |
| NaCl | 0.1% |
| (pH = 6.9). | |

100 ml of a BHI medium was inoculated with *Streptococcus pyogenes* ATCC 21060 and subjected to a static cultivation for eight hours at 37° C. to obtain a seed culture fluid. Then 1 l of the medium A was inoculated with 100 ml of the seed culture fluid thus obtained and subjected to a precultivation under the same condition as that of the seed culture fluid. Subsequently 8 l of the medium A was inoculated with the culture fluid thus obtained and cultured anaerobically with stirring in a jar fermentor (10 l) at a rate of 300 r.p.m. for 11.5 hours at 37° C. Then 1,000 u/ml of penicillin G was added and the cultivation was continued for additional five hours. The obtained culture broth was centrifuged to remove the bacterium.

The filtered culture broth contained 256 u/ml of the SPF-100.

EXAMPLE 2

9 l of medium B having the following composition was employed:

| | |
|---|---|
| meat extract | 1.0%, |
| polypeptone | 1.0%, |
| yeast extract | 0.25% and |
| NaCl | 0.1% |
| (pH = 7.0). | |

8 l of the medium B was inoculated with 1 l of a seed culture fluid in which Streptococcus pyogenes ATCC 21060 had been precultured in the similar manner as described in Example 1 and cultured anaerobically with stirring in a jar fermentor (10 l) at a rate of 300 r.p.m. for 11 hours at 37° C. Then 800 u/ml of penicillin G was added and the cultivation was continued for additional 5 hours. The obtained culture broth was centrifuged to remove the bacterium.

The filtered culture broth contained 351 u/ml of the SPF-100.

EXAMPLE 3

9 l of medium C having the following composition was employed:

| | |
|---|---|
| meat extract | 1%, |
| polypeptone | 1%, |
| yeast extract | 0.25% and |
| casamino acids | 0.25% |
| (pH = 6.2) | |

8 l of the medium C was inoculated with 1 l of a seed culture fluid in which Streptococcus pyogenes ATCC 21060 had been precultured in the similar manner as described in Example 1 and cultured anaerobically with stirring in a jar fermentor (10 l) at a rate of 300 r.p.m. for 14 hours at 37° C. Then 1000 u/ml of penicillin G was added and the cultivation was continued for additional 5 hours. The obtained culture broth was centrifuged to remove the bacterium.

The filtered culture broth contained 298 u/ml of the SPF-100.

EXAMPLE 4

9 l of medium D having the following composition was employed:

| | |
|---|---|
| meat extract | 0.5%, |
| polypeptone | 1.0%, |
| yeast extract | 0.25%, |
| casamino acids | 0.25% and |
| NaCl | 0.5% |
| (pH = 6.5) | |

8 l of the medium D was inoculated with 1 l of a seed culture fluid in which Streptococcus pyogenes ATCC 21060 had been precultured in the similar manner as described in Example 1 and cultured anaerobical with stirring in a jar fermentor (10 l) at a rate of 300 r.p.m. for 15.5 hours at 37° C. Then 1200 u/ml of penicillin G was added and the cultivation was continued for additional 5 hours. The obtained culture broth was centrifuged to remove the bacterium.

The filtered culture broth contained 285 u/ml of the SPF-100.

EXAMPLE 5

9 l of medium E having the following composition was employed:

| | |
|---|---|
| yeast extract | 3.0% |
| (pH = 6.5). | |

8 l of the medium E was inoculated with 1 l of a seed culture fluid in which Streptococcus pyogenes ATCC 21060 had been precultured in the similar manner as described in Example 1 and cultured anaerobically with stirring in a jar fermentor (10 l) at a rate of 300 r.p.m. for 15 hours at 37° C. Then 1000 u/ml of penicillin G was added and the cultivation was continued for additional 5 hours. The obtained culture broth was centrifuged to remove the bacterium.

The filtered culture broth contained 182 u/ml of SPF-100.

EXAMPLE 6

9 l of medium F having the following composition was employed:

| | |
|---|---|
| maltose | 0.3%, |
| meat extract | 2.0%, |
| polypeptone | 1.0% and |
| yeast extract | 0.25% |
| (pH = 7.0). | |

8 l of the medium F was inoculated with 1 l of a seed culture fluid in which Streptococcus pyogenes ATCC 21060 had been precultured in the similar manner as described in the Example 1 and cultured anaerobically with stirring in a jar fermentor (10 l) at a rate of 300 r.p.m. for 10.5 hours at 37° C. Then 1000 u/ml of penicillin G was added and the cultivation was continued for additional 5 hours. The obtained culture broth was centrifuged to remove the bacterium.

The filtered culture broth contained 250 u/ml of the SPF-100.

EXAMPLE 7

9 l of medium G having the following composition was employed:

| | |
|---|---|
| meat extract | 1.0%, |
| polypeptone | 1.0% and |
| NaCl | 0.5% |
| (pH = 7.0). | |

8 l of the medium G was inoculated with 1 l of a seed culture fluid in which Streptococcus pyogenes ATCC 21060 had been precultured in the similar manner as described in Example 1 and cultured anaerobically with stirring in a jar fermentor (10 l) at a rate of 300 r.p.m. for 15 hours at 37° C. Then 1000 u/ml of penicillin G was added and the cultivation was continued for additional 5 hours. The obtained culture broth was centrifuged to remove the bacterium.

The filtered culture broth contained 200 u/ml of the SPF-100.

EXAMPLE 8

9 l of medium H having the following composition was employed:

| | |
|---|---|
| meat extract | 1.0%, |
| polypeptone | 1.0%, |
| yeast extract | 0.25% |
| casamino acids | 0.25% and |
| NaCl | 0.1% |
| (pH = 7.0). | |

8 l of the medium H was inoculated with 1 l of a seed culture fluid in which *Streptococcus sp.* ATCC 21597 had been precultured in the similar manner as described in Example 1 and cultured anaerobically with stirring in a jar fermentor (10 l) at a rate of 300 r.p.m. for 11 hours at 37° C. Then 1000 u/ml of pecicillin G was added and the cultivation was continued for additional 5 hours. The obtained culture broth was centrifuged to remove the bacterium.

The filtered culture broth contained 250 u/ml of the SPF-100.

EXAMPLE 9

9 l of medium I having the following composition was employed:

| | |
|---|---|
| meat extract | 0.5% |
| polypeptone | 1%, |
| yeast extract | 0.25% |
| casamino acids | 0.25% and |
| NaCl | 0.1% |
| (pH = 6.5) | |

8 l of the medium I was inoculated with 1 l of a seed culture fluid in which *Streptococcus pyogenes* ATCC 21546 had ben precultured in the similar manner as described in Example 1 and cultured anaerobically with stirring in a jar fermentor (10 l) at a rate of 300 r.p.m. for 11 hours at 37° C. Then 1000 u/ml of penicillin G was added and the cultivation was continued for additional 5 hours. The obtained culture broth was centrifuged to remove the bacterium.

The filtered culture broth contained 340 u/ml of the SPF-100.

EXAMPLE 10

9 l of medium J having the following composition was employed:

| | |
|---|---|
| meat extract | 2.0%, |
| polypeptone | 1.0%, |
| yeast extract | 0.25%, |
| casamino acids | 0.25% and |
| NaCl | 0.5% |
| (pH = 6.5) | |

8 l of the medium J was inoculated with 1 l of a seed culture fluid in which *Streptococcus pyogenes* ATCC 21547 had been precultured in the similar manner as described in Example 1 and cultured anaerobically with stirring in a jar fermentor (10 l) at a rate of 300 r.p.m. for eight hours at 37° C. Then 1500 u/ml of penicillin G was added and the cultivation was continued for additional 5 hours. The obtained culture broth was centrifuged to remove the bacterium.

The filtered culture broth contained 320 u/ml of the SPF-100.

EXAMPLE 11

9 l of medium K having the following composition was employed:

| | |
|---|---|
| maltose | 0.3%, |
| polypeptone | 1.0% and |
| yeast extract | 0.25% |
| (pH = 6.8). | |

8 l of the medium K was inoculated with 1 l of a seed culture fluid in which *Streptococcus pyogenes* ATCC 21548 had been precultured in the similar manner as described in the Example 1 and cultured anaerobically with stirring in a jar fermentor (10 l) at a rate of 300 r.p.m. for five hours at 37° C. Then 1000 u/ml of penicillin G was added and the cultivation was continued for additional 5 hours. The obtained culture broth was centrifuged to remove the bacterium.

The filtered culture broth contained 270 u/ml of the SPF-100.

EXAMPLE 12

5 l of the filtered culture broth obtained in the cultivation in Example 4 contained $143 \times 10^4$ u of the SPF-100.

Ammonium sulfate was added to the filtered culture broth and a fraction of 50 to 90% in the degree of saturation was recovered to obtain a precipitate. This precipitate contained $118 \times 10^4$ u of the SPF-100.

The whole precipitate was dissolved in 300 ml of a phosphate buffer solution and the solution thus obtained was introduced into a DEAE-cellulose column ($5 \times 70$ cm) to thereby absorb the SPF-100. Then it was eluted with a 0.3M NaCl solution stepwise to fractionate the active fraction. The activity thus obtained was $102.2 \times 10^4$ u.

Then the active fraction was introduced into a DEAE-Sephadex A-25 column ($2.6 \times 70$ cm) to absorb the active fraction. Then it was eluted while raising the concentration of common salt in the phosphate buffer solution linearly to recover the active fraction. The activity thus obtained was $79.3 \times 10^4$ u.

Furthermore, the eluate was concentrated and introduced into a column ($2.6 \times 100$ cm) of a gel filtration material Toyopearl HW-50F to absorb. Subsequently it was eluted with a 1/100M phospate buffer solution ($KH_2PO_4$—$Na_2HPO_4$) to recover an active fraction which was referred to SPF-100. The activity thus obtained was $71.1 \times 10^4$ u.

The eluate thus obtained was lyophilized to obtain 1780 mg of SPF-100 in the form of a pale yellow powder.

The SPF-100 obtained in Example 12 was subjected to in vitro, in vitro/in vivo and in vivo tests as a test agent to examine its tumoricidal effect.

TEST EXAMPLE 1 (in vitro test)

Tumoricidal activity of the test agent in vitro was determined according to the determination of the degree of cellular growth.

P-388 and L-1210 Lymphomas obtained by subculture of isologously implanted tumors of DEA/Two lines mice were employed as cancerous cells. These lymphomas were respectively suspended in an RPMI 1640 medium containing $5 \times 10^{-5}$M of 2-mercapto ethanol and 50 mg /l of kanamycin and to which 10% FCS was added. Then 1 ml of this medium was injected into a Falcon 3047 plate at a concentration of the cancerous cells of $5 \times 10^4$ cells/well. Subsequently a particular amount of the test agent which was dissolved or suspended in 1 ml of the medium was injected into the abovementioned medium and cultured in the presence of 5% of $CO_2$ at 37° C. 48 hours after the injection of the test agent, vital staining with nigrosine was carried out and the degree of cellular growth was determined by the following equation:

$$\text{Degree of cellular growth (\%)} = \frac{\text{Number of cells in each test group}}{\text{Number of cells in the control group}} \times 100.$$

Table 1 shows the result.

TABLE 1

| Dose of SPF-100 | Degree of Cellular Growth (%) | |
|---|---|---|
| | Lymphoma | |
| ($\times 10^2$ u) | P-388 | L-1210 |
| 4.7 | 92.0 | 98.6 |
| 9.3 | 83.9 | 94.6 |
| 18.6 | 78.2 | 68.0 |
| 37.2 | 57.2 | 49.2 |

TEST EXAMPLE 2 (in vitro/in vitro test)

Tumoricidal activity of the test agent in vitro/in vivo was determined by the use of ddy female mice of four or five weeks of age.

Ehrlich ascites cancerous cells which were used as cancerous cells were suspended in a KRP buffer solution, then admixed with a particular amount of the test agent and incubated for 60 or 80 min at 37° C. The mice were intraperitoneally inoculated with 0.2 ml portions (0.2 ml/mouse) of the medium containing $4 \times 10^6$ or $8 \times 10^6$ of cancerous cells to observe the number of vital mice. Tables 2 and 3 show the results.

TABLE 2

Tumoricidal Activity of SPF-100
(Number of vital mice)
(ddy female mouse of five weeks of age)

| Dose (u) | Day | | | | |
|---|---|---|---|---|---|
| | 0 | 10 | 15 | 20 | 25 |
| Control (0) | 8/8 | 8/8 | 7/8 | 1/8 | 0/8 |
| $0.625 \times 10^2$ | 8/8 | 8/8 | 8/8 | 6/8 | 3/8 |
| $10 \times 10^2$ | 8/8 | 8/8 | 8/8 | 6/8 | 2/8 |

In Tables 2 to 5 figures indicate the number of vital mice/the number of employed mice.

TABLE 3

Tumoricidal Activity of SPF-100
(Number of vital mice)
(ddy female mice of four weeks of age)

| Dose (u) | Day | | | | |
|---|---|---|---|---|---|
| | 0 | 10 | 15 | 20 | 25 |
| Control (0) | 8/8 | 8/8 | 2/8 | 0/8 | 0/8 |
| $20 \times 10^2$ | 8/8 | 8/8 | 8/8 | 8/8 | 6/8 |

Test Example 3 (in vivo test)

Tumoricidal activity of the test agent in vivo was determined by the use of CRJ-CD-1 (ICR) male mice of seven weeks of age.

Sarcoma-180 ascites cancerous cells which were used as cancerous cells were suspended in a Hank's solution. Then the mice were inoculated with 0.1 ml portions of the suspension containing $2 \times 10^6$ of cancerous cells intraperitoneally.

A particular amount of the test agent was intraperitoneally administered to the mice once a day for five consecutive days before the inoculation of the cancerous cells or once a day for respectively five consecutive days before and after the inoculation of the cancerous cells to observe the number of vital mice. Tables 4 and 5 show the results.

TABLE 4

Tumoricidal Activity of SPF-100
(Number of vital mice)
(administered before the inoculation)

| Dose (u) | Day | | | | |
|---|---|---|---|---|---|
| | 0 | 10 | 15 | 20 | 25 |
| Control (u) | 8/8 | 8/8 | 8/8 | 2/8 | 0/8 |
| $1 \times 10^2$ | 8/8 | 8/8 | 8/8 | 5/8 | 4/8 |
| $100 \times 10^2$ | 8/8 | 8/8 | 8/8 | 4/8 | 2/8 |

TABLE 5

(administered before and after the inoculation)

| Dose (u) | Day | | | | |
|---|---|---|---|---|---|
| | 0 | 10 | 15 | 20 | 25 |
| Control (0) | 8/8 | 8/8 | 8/8 | 3/8 | 1/8 |
| $1 \times 10^2$ | 8/8 | 8/8 | 8/8 | 7/8 | 4/8 |
| $20 \times 10^2$ | 8/8 | 8/8 | 7/8 | 5/8 | 2/8 |

EXAMPLE 13

1000 mg of the SPF-100 obtained in the similar manner as described in Example 8 in the form of a pale yellow powder was dissolved in 30 ml of a phosphate buffer solution and poured into a Sephadex A-25 column ($2.6 \times 70$ cm) to absorb the SPF-100. Then it was eluted while raising the concentration of common salt in the phosphate buffer solution linearly to obtain an active fraction. Subsequently the obtained whole active fraction was concentrated to 5 ml and poured into a column of a gel filtration material Toyopearl HW-50F ($2 \times 100$ cm) and eluted with a phosphate buffer solution to obtain an active fraction containing a substance with a molecular weight of about 500 to about 7000. The active fraction was lyophilized to obtain 350 mg of a white powder which was referred to SPF-1.

Physicochemical properties of the SPF-1 were as follows:

1. Elemental analysis

C: 41.26%, H: 4.91%, N: 6.52%, O: 44.46% and Ash: 2.85%

36.64%  4.10%  5.40%  51.56%  2.30%

2. Molecular weight

Approximately 500 to 7,000 as determined by gel filtration

3. Decomposition point

It turned to brown at 170° C. and to black at 200° C. and decomposed.

Figure 3:
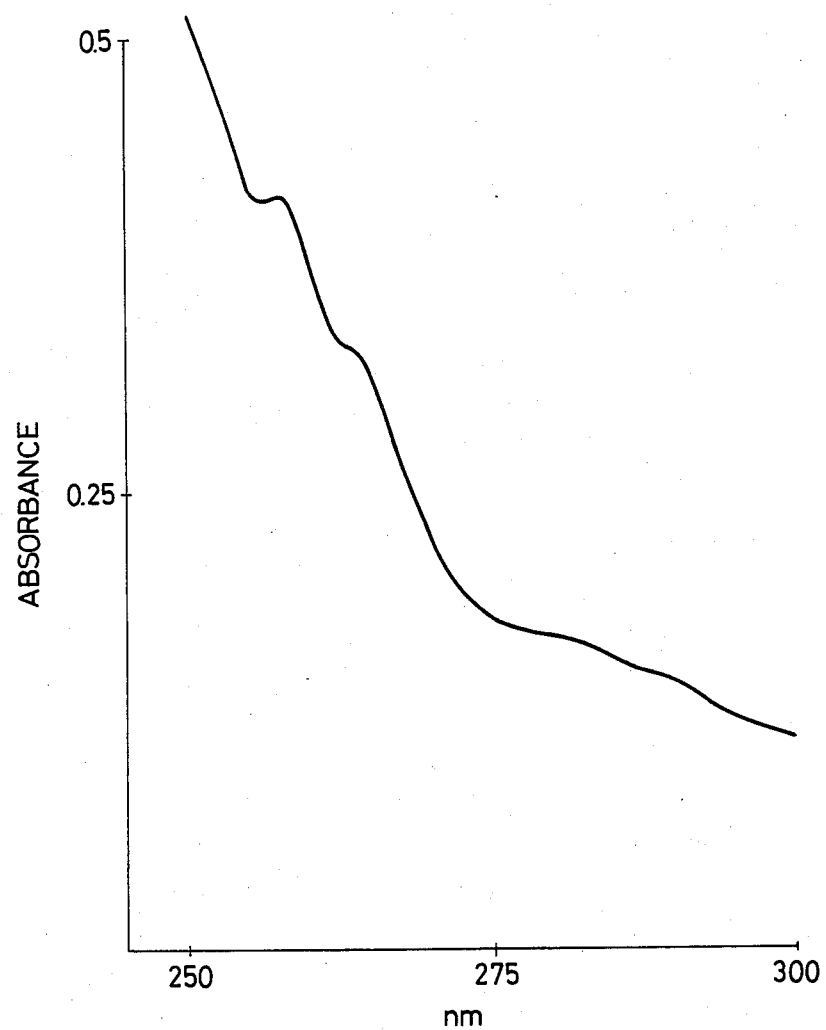
Figure 4:
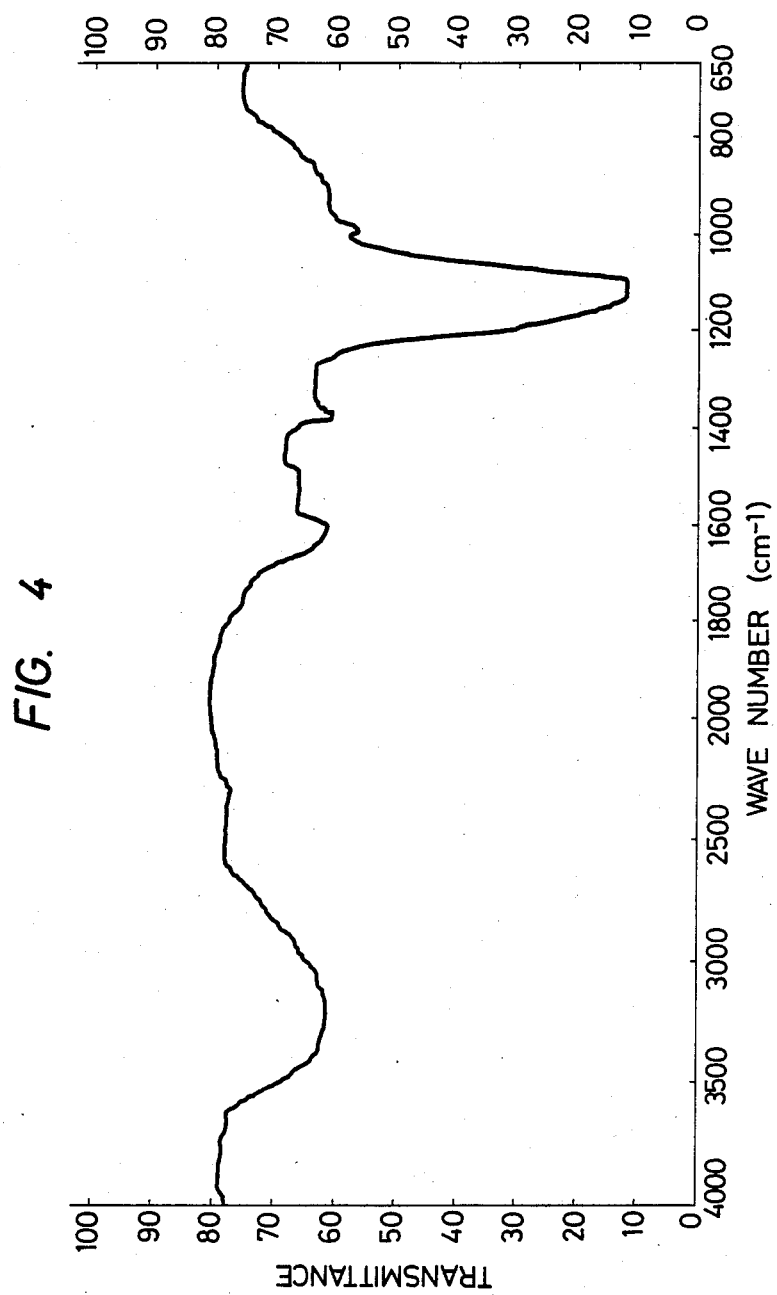
FIG. 4 shows an infrared absorption spectrum of SPF-1.

4. Specific rotation
  $[\alpha]_D^{20} = +63.3$ to $64.3°$ (c=1.04).
5. Ultraviolet absorption spectrum
  FIG. 3 shows an ultraviolet absorption spectrum of a 3.3% aqueous solution, which is characterized by the absorptions at 257, 265, 280 and 287 nm.
6. Infrared absorption spectrum
  FIG. 4 shows an infrared absorption spectrum.
7. Solubility in solvents
  It was soluble in water but insoluble in solvents including methanol, ethanol, n-butanol, isobutanol, n-propanol, n-hexane, chloroform, acetone, methyl isobutyl ketone and ethyl ether.
8. Acidity
  The pH value of an 0.85% aqueous solution was 6.5.
9. Form
  White powder
10. Color reactions
  ninhydrin reactions: +,
  biuret reaction: +,
  Molisch reaction: —,
  Dische reaction: —,
  anthrone reaction: — and
  cysteine sulfate reaction: —.
11. Stability
  It can be established by adding L-cysteine, dithiothreitol (DTT), glycerol, albumin, globulin, $(NH_4)_2SO_4$, common salt or the like.

EXAMPLE 14

In the similar manner as described in Example 13 was obtained an active fraction containing a substance with a molecular weight of about 7000 to about 25,000. The active fraction was lyophilized to obtain 380 mg of a pale yellow powder which was referred to SPF-2.

Physicochemical properties of the SPF-2 were as follows:
1. Elemental analysis

C: 53.64%, H: 5.98%, N: 11.63%, O: 26.05% and Ash: 2.70%

48.57%   5.02%   10.50%   33.73%   2.25%

Figure 5:
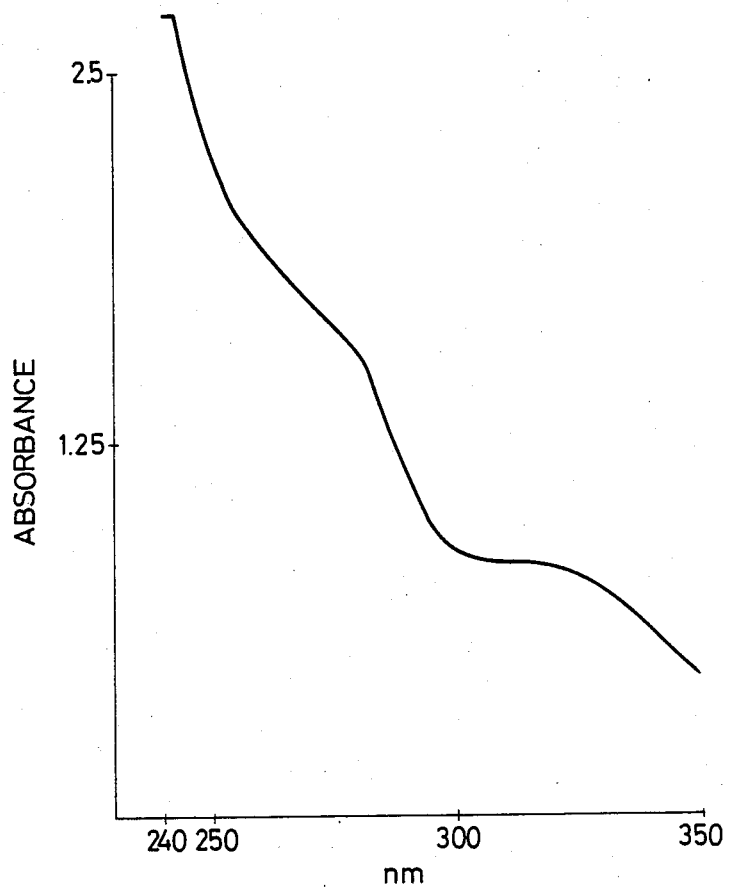
Figure 6:
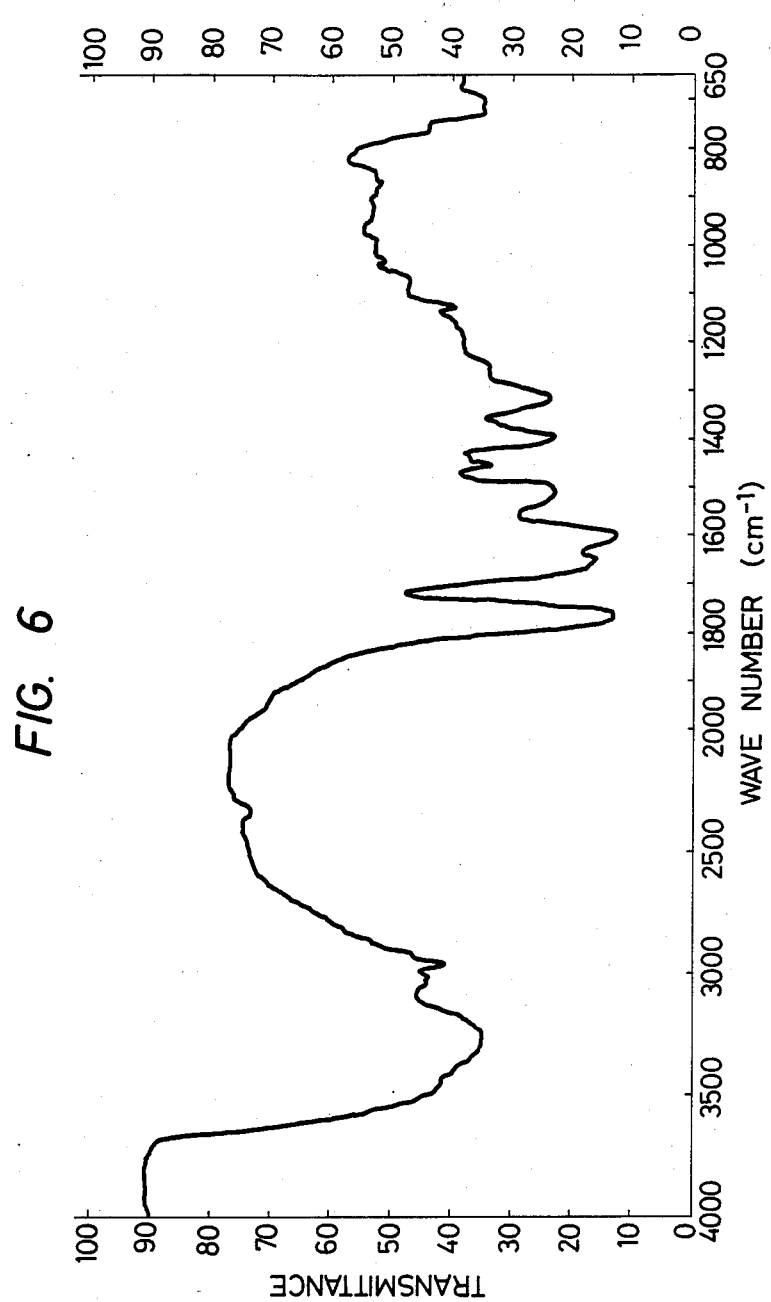
FIG. 6 shows an infrared absorption spectrum of SPF-2.

2. Molecular weight
  Approximately 7,000 to 25,000 as determined by gel filtration
3. Decomposition point
  It turned to brown at 160° C. and to black at 200° C. and decomposed.
4. Specific rotation
  $[\alpha]_D^{20} = +30.7°$ (c=1.00).
5. Ultraviolet absorption spectrum
  FIG. 5 shows an ultraviolet absorption spectrum of a 0.2% aqueous solution, which is characterized by the absorptions at 257, 265, 273, 280, 287 and 325 nm.
6. Infrared absorption spectrum
  FIG. 6 shows an infrared absorption spectrum.
7. Solubility in solvents
  It was soluble in water, partly soluble in methanol and ethanol and hardly or not soluble in solvents including n-butanol, isobutanol, n-propanol, n-hexane, chloroform, acetone, methyl isobutyl ketone and ethyl ether.
8. Acidity
  The pH value of a 1.0% aqueous solution was 6.5.
9. Form
  Pale yellow powder
10. Color reactions
  ninhydrin reaction: +,
  biuret reaction: +,
  Molisch reaction: —,
  Dische reaction: —,
  anthrone reaction: — and
  cysteine sulfate reaction: —.
11. Stability
  It can be stabilized by adding L-cysteine, dithiothreitol (DTT), glycerol, albumin, globulin, α- and β-cyclodextrine, $(NH_4)_2SO_4$, common salt or the like.

EXAMPLE 15

5 l of the filtered culture broth obtained in Example 8 was purified in the similar manner as described in Example 12 to obtain 1460 mg of a pale yellow powdery SPF-100.

1000 mg of the powder was treated to obtain 330 mg of the SPF-1 in the same manner as in Example 13 and 370 mg of the SPF-2 in the same manner as in Example 14.

EXAMPLE 16

5 l of the filtred culture broth obtained in Example 9 was purified in the similar manner as described in Example 12 to obtain 1650 mg of a pale yellow powdery SPF-100.

1000 mg of the powder was treated to obtain 315 mg of the SPF-1 in the same manner as in Example 13 and 390 mg of the SPF-2 in the same manner as in Example 14.

EXAMPLE 17

3 l of medium L having the following composition was employed:

| | |
|---|---|
| BHI (pH = 7.4) | 3.7% |

100 ml of a BHI medium was inoculated with *Streptococcus pyogenes* ATCC 21060 and subjected to a static cultivation for eight hours at 37° C. to obtain a seed culture fluid. 300 ml of the seed fluid was inoculated into 3 l of the medium L and cultured anaerobically with stirring in a 3 l flask at 37° C. for 11.5 hours. Then 500 μg/ml of cephalosporin C was added and the cultivation was continued for additional five hours. The obtained culture broth was centrifuged to remove the bacterium.

The filtered culture broth contained 120 u/ml of the SPF-100.

3 l of the filtered culture broth was purified in the similar manner as described in Example 12 to obtain 530 mg of a pale yellow powdery SPF-100.

500 mg of the powder was treated to obtain 110 mg of the SPF-1 in the same manner as in Example 13 and 160 mg of the SPF-2 in the same manner as in Example 14.

We claim:
1. A substance called SPF-100 recovered from a culture broth of *Streptococcus pyogenes* and having the following physicochemical properties:
(1) Elemental analysis
  C: 46.42 to 43.69%, H: 5.94 to 4.85%, N: 11.42 to 9.50%, O: 33.82 to 39.69% and Ash: 2.40 to 2.27%
(2) Molecular weight
  Approximately 500 to 25,000 as determined by gel filtration
(3) Decomposition point

It turns to brown at 160° C. and to black at 200° C. and decomposes (4) Specific rotation $[\alpha]_D^{20} = +45.0°$ (c=1.00)

(5) Ultraviolet absorption spectrum

FIG. 1 shows an ultraviolet spectrum of a 0.1% aqueous solution, which is characterized by the absorptions at 257, 265, 280, 287 and 325 nm (6) Infrared absorption spectrum FIG. 2 shows an infrared absorption spectrum (7) Solubility in solvents It is soluble in water, partly soluble in methanol and ethanol and hardly or not soluble in solvents including n-butanol, isobutanol, n-propanol, n-hexane, chloroform, acetone, methyl isobutyl ketone and ethyl ether (8) Acidity The pH value of a 1.0% aqueous solution is 6.5

(9) Form

Pale yellow powder

(10) Color reactions ninhydrin reaction: +,
biuret reaction: +,
Molisch reaction: −,
Dische reaction: −,
anthrone reaction: − and
cysteine sulfate reaction: −

(11) Stability

It can be stabilized by adding L-cysteine, dithiothreitol (DTT), glycerol, albumin, globulin, α- and β-cyclodextrine, $(NH_4)_2SO_4$, common salt or the like.

2. A process for preparing SPF-100 as defined in claim 1 comprising culturing a *Streptococcus pyogenes* selected from the group consisting of

*Streptococcus pyogenes* ATCC 21060

*Streptococcus pyogenes* ATCC 21546

*Streptococcus sp.* ATCC 21597

*Streptococcus pyogenes* ATCC 21547 and

*Streptococcus pyogenes* ATCC 21548 in a medium containing carbon sources or nitrogen sources and nutrient sources under anaerobic conditions at a pH of 6.0 to 8.0 at 30° to 40° C.;

adding penicillin G in an amount of 100 to 7000 units/ml of the medium or cephalosporin C in an amount of 10 to 4000 μg/ml of the medium 3–15 hours after initiation of logarithmic growth phase;

continuing culturing for 1 to 20 hours; and recovering the substance called SPF-100 from the culture broth.

* * * * *